United States Patent [19]

Brouwer et al.

[11] Patent Number: 4,609,676

[45] Date of Patent: Sep. 2, 1986

[54] BENZOYLUREA COMPOUNDS, AND PESTICIDAL AND PHARMACEUTICAL COMPOSITIONS COMPRISING SAME

[75] Inventors: Marius S. Brouwer; Arnoldus C. Grosscurt, both of Weesp, Netherlands

[73] Assignee: Duphar International Research B.V., Weesp, Netherlands

[21] Appl. No.: 759,321

[22] Filed: Jul. 26, 1985

Related U.S. Application Data

[62] Division of Ser. No. 572,145, Jan. 19, 1984, Pat. No. 4,550,202.

[30] Foreign Application Priority Data

Jan. 24, 1983 [NL] Netherlands ............... 8300236

[51] Int. Cl.$^4$ ............ A01N 43/40; A01N 47/28
[52] U.S. Cl. ............... 514/594; 514/357; 514/584
[58] Field of Search .......... 514/584, 594, 357

[56] References Cited

U.S. PATENT DOCUMENTS 3,917,690 11/1975 Weber et al. ............ 564/23
4,327,213 4/1982 Van Zorge ............ 544/336

FOREIGN PATENT DOCUMENTS 2106499 4/1983 United Kingdom .

*Primary Examiner*—Allen J. Robinson
*Attorney, Agent, or Firm*—Stevens, Davis, Miller & Mosher

[57] ABSTRACT

The invention relates to new benzoylurea compounds of the general formula

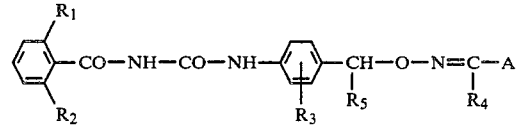

wherein
$R_1$ is a halogen atom,
$R_2$ is a hydrogen atom or a halogen atom,
$R_3$ is a hydrogen atom or represents 1 or 2 substituents which are selected from the group consisting of chlorine, methyl and trifluoromethyl,
$R_4$ is a hydrogen atom, an alkyl group having 1-6 carbon atoms or a cycloalkyl group having 3-6 carbon atoms,
$R_5$ is a hydrogen atom or an alkyl group having 1-4 carbon atoms, and
A is a phenyl group or a heteroaryl group having 1 or 2 nitrogen atoms, which groups may be substituted with 1-3 substituents which are selected from the group consisting of halogen, and alkyl, alkoxy, haloalkyl and haloalkoxy having 1-4 carbon atoms.

The compounds have an insecticidal and acaricidal activity. After having been processed to compositions, the compounds may be used for control of insects and/or mites in a dosage from 1 to 5000 g of active substance per hectare. In addition the compounds have an anti-tumor activity and may be used in pharmaceutical compositions.

4 Claims, No Drawings

BENZOYLUREA COMPOUNDS, AND PESTICIDAL AND PHARMACEUTICAL COMPOSITIONS COMPRISING SAME

This is a division of application Ser. No. 572,145 filed Jan. 19, 1984, now U.S. Pat. No. 4,550,202.

The invention relates to new benzoylurea compounds and to a method of preparing these compounds. The invention also relates to compositions with insecticidal and acaricidal activity which comprise these compounds and to the use of these compositions for controlling insects and/or mites. The invention further relates to pharmaceutical compositions comprising same compounds and to the use of these compositions for combating tumors.

N-Benzoyl-N'-phenylurea compounds having insecticidal activity are known from Applicants' Netherlands patent application No. 7105350. In Chem. Abstracts 91, 20141 (1979) benzoylurea compounds are described having both an insecticidal and an acaricidal activity, for example N-(2,6-difluorobenzoyl)-N'-(4-benzyloxyphenyl)urea. This compound, however, proves to have no marked acaricidal activity in practically acceptable dosages.

It has surprisingly been found that benzoylurea compounds of the general formula

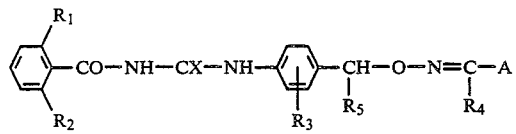

wherein
- $R_1$ is a halogen atom,
- $R_2$ is a hydrogen atom or a halogen atom,
- $R_3$ is a hydrogen atom or represents 1 or 2 substituents which are selected from the group consisting of chlorine, methyl or trifluoromethyl,
- $R_4$ is a hydrogen atom, an alkyl group having 1–6 carbon atoms or a cycloalkyl group having 3–6 carbon atoms,
- $R_5$ is a hydrogen atom or an alkylgroup having 1–4 carbon atoms,
- A is a phenyl group or a heteroaryl group having 1 or nitrogen atoms, which groups may be substituted with 1–3 substituents which are selected from the group consisting of halogen, and alkyl, alkoxy, haloalkyl and haloalkoxy having 1–4 carbon atoms, and
- X is an oxygen or sulphur atom, not only have strong insecticidal properties, but also show an interesting acaricidal activity.

Of the above compounds especially those compounds prove to have a high acaricidal activity, which correspond to the general formula

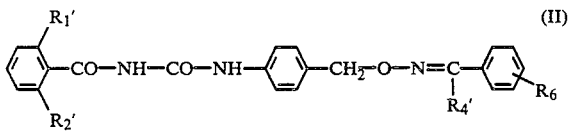

wherein
- $R'_1$ and $R'_2$ are both fluorine atoms, or wherein $R'_1$ is a chlorine atom and $R'_2$ is a hydrogen atom,
- $R'_4$ is a n-propyl, isopropyl or cyclopropyl group, and
- $R_6$ is a hydrogen atom or represents 1–2 substituents which are selected from the group consisting of halogen, and alkyl, alkoxy, haloalkyl and haloalkoxy having 1–4 carbon atoms.

Of these last-mentioned compounds N-(2,6-difluorobenzoyl)-N'-[4-(α-cyclopropyl-4-chlorobenzylideneaminooxymethyl)phenyl]urea (1) proves to be eminently suitable to be applied in controlling insects and mites.

Other examples of new benzoylurea compounds having insecticidal and acaricidal activity, according to the invention are:

(2) N-(2,6-difluorobenzoyl)-N'-[4-(1-phenylpropylideneaminooxymethyl)phenyl]urea,
(3) N-(2-chlorobenzoyl)-N'-]4-(1-phenylbutylideneaminooxymethyl)phenyl]-urea,
(4) N-(2,6-difluorobenzoyl)-N'-[4-(1-phenylbutylideneaminooxymethyl)phenyl]urea,
(5) N-(2-chlorobenzoyl)-N'-[4-(1-phenyl-2-methylpropylideneaminooxymethyl)phenyl]urea,
(6) N-(2,6-difluorobenzoyl)-N'-[4-{1-(4-chlorophenyl)propylideneaminooxymethyl}phenyl]urea,
(7) N-(2-chlorobenzoyl)-N'-[4-{1-(4-chlorophenyl)butylideneaminooxymethyl}phenyl]urea,
(8) N-(2,6-difluorobenzoyl)-N'-[4-{1-(4-chlorophenyl)butylideneaminooxymethyl}phenyl]urea.
(9) N-(2-chlorobenzoyl)-N'-[4-{1-(4-chlorophenyl)-2-methylpropylideneaminooxymethyl}phenyl]urea,
(10) N-(2,6-difluorobenzoyl)-N'-[4-{1-(4-chlorophenyl)-2-methylpropylideneaminooxymethyl}phenyl]urea,
(11) N-(2-chlorobenzoyl)-N'-[4-{1-(2,4-dichlorophenyl)pentylideneaminooxymethyl}phenyl]urea,
(12) N-(2,6-difluorobenzoyl)-N'-[4-{1-(2,4-dichlorophenyl)pentylideneaminooxymethyl}phenyl]urea,
(13) N-(2-chlorobenzoyl)-N'-[4-{1-(3,4-dichlorophenyl)butylideneaminooxymethyl}phenyl]urea,
(14) N-(2,6-difluorobenzoyl)-N'-[4-{1-(3,4-dichlorophenyl)butylideneaminooxymethyl}phenyl]urea,
(15) N-(2-chlorobenzoyl)-N'-[4-{1-(pyridyl-2)butylideneaminooxymethyl}phenyl]urea,
(16) N-(2,6-difluorobenzoyl)-N'-[4-{1-(pyridyl-2)butylideneaminooxymethyl}phenyl]urea,
(17) N-(2-chlorobenzoyl)-N'-[4-(α-cyclopropyl-4-chlorobenzylideneaminooxymethyl)phenyl]urea,
(18) N-(2,6-difluorobenzoyl)-N'-[4-{1-(4-chlorophenyl)ethylideneaminooxymethyl}phenyl]urea,
(19) N-(2-chlorobenzoyl)-N'-[4-(1-phenylpropylideneaminooxymethyl)phenyl]urea,
(20) N-(2,6-difluorobenzoyl)-N'-(4-benzylideneaminooxymethylphenyl)urea,
(21) N-(2,6-difluorobenzoyl)-N'-[4-{1-(4-methylphenyl)pentylideneaminooxymethyl}phenyl]urea,
(22) N-(2-chlorobenzoyl)-N'-[4-{1-(2,4-dichlorophenyl)butylideneaminooxymethyl}phenyl]urea,
(23) N-(2,6-difluorobenzoyl)-N'-[4-{1-(2,4-dichlorophenyl)butylideneaminooxymethyl}phenyl]urea,
(24) N-(2,6-difluorobenzoyl)-N'-[4-{1-(3,4-dichlorophenyl)butylideneaminooxymethyl}phenyl]thiourea,
(25) N-(2-chlorobenzoyl)-N'-[3-chloro-4-{1-(2,4-dichlorophenyl)butylideneaminooxymethyl}phenyl]urea,

(26) N-(2,6-difluorobenzoyl)-N'-[3-chloro-4-{1-(2,4-dichlorophenyl)butylideneaminooxymethyl}phenyl]urea,
(27) N-(2-chlorobenzoyl)-N'-[4-{1-(4-methoxyphenyl)butylideneaminooxymethyl}phenyl]urea,
(28) N-(2-chlorobenzoyl)-N'-[3-chloro-4-(1-phenylbutylideneaminooxymethyl)phenyl]urea,
(29) N-(2,6-difluorobenzoyl)-N'-[3-chloro-4-(1-phenylbutylideneaminooxymethyl)phenyl]urea,
(30) N-(2-chlorobenzoyl)-N'-[4-{1-(4-methylphenyl)pentylideneaminooxymethyl}phenyl]urea,
(31) N-(2,6-difluorobenzoyl)-N'-[4-{1-(4-trifluoromethylphenyl)-2-methylpropylideneaminooxymethyl}phenyl]urea,
(32) N-(2,6-difluorobenzoyl)-N'-[4-{1-(4-bromophenyl)-2-methylpropylideneaminooxymethyl}phenyl]urea,
(33) N-(2-chlorobenzoyl)-N'-[4-{1-(1-phenylbutylideneaminooxy)ethyl}phenyl]urea,
(34) N-(2,6-difluorobenzoyl)-N'-[4-{1-(1-phenylbutylideneaminooxy)ethyl}phenyl]urea,
(35) N-(2,6-difluorobenzoyl)-N'-[4-(1-phenyl-2-methylpropylideneaminooxymethyl)phenyl]urea, and
(36) N-(2-chlorobenzoyl)-N'-[4-{1-(4-chlorophenyl)propylideneaminooxymethyl}phenyl]urea.

The new benzoylurea compounds of the invention can occur in two stereoisomers, viz. the syn- and the anti-form, while, of course, also mixtures of these stereoisomers are possible in all ratios. If desired, these stereoisomers can be separated from each other by using technics which are known for this purpose, such as recrystallization and/or column chromatography. The activity may be influenced by the sterical configuration.

The substances according to the invention may be used for the control of mites and insects in agriculture and horticulture, in forests and in surface water, as well as for the protection of textile against attack by, for example in stored cereals, and against mites and insects in the veterinary and medical-hygienic sector.

The substances according to the invention can also be used for the control of insects living in the manure of warm-blooded animals, such as cows, pigs and hens. For this application, the active compounds can be administered orally to the animals, for example, mixed through the food, so that they land in the manure after some time ("through-feeding").

The compounds according to the invention are particularly active against larvae and eggs of mites and insects. In principle, the compounds may be used against all insects mentioned in Pestic. Sci. 9, 373–386 (1978).

In addition it has been found, that the compounds of the invention have cytostatic or anti-tumor activity, in that they show an inhibiting effect on the growth of tumors. For use in pharmaceutical compositions for combating tumors in living beings the compounds of the invention should be incorporated into pharmaceutically acceptable carriers.

For practical application the substances in accordance with the invention are usually processed to compositions. In such compositions the active substance is mixed with solid carrier material or dissolved or dispersed in liquid carrier material, if desired in combination with auxiliary substances, for example, emulsifiers, wetting agents, dispersible agents and stabilizers.

Examples of compositions according to the invention are aqueous solutions and dispersions, oily solutions and oily dispersions, solutions in organic solvents, pastes, dusting powders, dispersible powders, miscible oils, granules, pellets, invert emulsions, aerosol compositions and fumigating candles.

Dispersible powders, pastes and miscible oils are compositions in concentrate form which are diluted prior to or during use.

The invert emulsions and solutions in organic solvents are mainly used in air application; namely when large areas are treated with a comparatively small quantity of composition. The invert emulsion can be prepared shortly before or even during spraying in the spraying apparatus by emulsifying water in an oily solution or an oily dispersion of the active substance. The solutions of the active substance in organic solvents may be provided with a phytotoxicity-reducing substance, for example, wool fat, wool fatty acid or wool fatty alcohol.

A few forms of composition will be described in greater detail hereinafter by way of example.

Granular compositions are prepared by taking up, for example, the active substance in a solvent or dispersing it in a diluent and impregnating the resulting solution/suspension, if desired in the presence of a binder, on granular carrier material, for example porous granules (for example pumice and attaclay), mineral non-porous granules (sand or ground marl), organic granules (for example, dried coffee grounds, cut tobacco stems and ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers, and glomulating the mixture then with liquid to the desired particle size.

Dusting powders can be obtained by intimately mixing the active substance with an inert solid powdered carrier material, for example, talcum.

Dispersible powders are prepared by mixing 10 to 80 parts by weight of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example the lignine sulphonates or alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally, if desired, other additives.

For the preparation of miscible oils the active compound is dissolved in a suitable solvent which preferably is poorly water-miscible, and one or more emulsifiers are added to this solution. Suitable solvents are, for example, xylene, toluene, petroleum distillates which are rich in aromates, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight. In addition to a miscible oil may also be mentioned as a liquid and highly concentrated primary composition a solution of the active substance in a readily water-miscible liquid, for example, a glycol, or glycol ether, to which solution a dispersion agent and, if desired, a surface-active substance has been added. When diluting with water shortly before or during spraying, an aqueous dispersion of the active substance is then obtained.

An aerosol composition according to the invention is obtained in the usual manner by incorporating the active substance, if desired in a solvent, in a volatile liquid to be used as a propellant, for example, a mixture of chlorine-fluorine derivatives of methane and ethane, a mixture of lower hydrocarbons, dimethyl ether, or gases such as carbon dioxide, nitrogen and nitrous oxide.

Fumigating candles or fumigating powders, i.e. compositions which, while burning, can generate a pesticidal smoke, are obtained by taking up the active substance in a combustible mixture which may contain as a fuel a sugar or a wood, preferably in a ground form, a substance to maintain combustion, for example, ammonium nitrate or potassium chlorate, and furthermore a substance to delay combustion, for example, kaolin, bentonite and/or colloidal silicic acid.

In addition to the above-mentioned ingredients, the agents according to the invention may also contain other substances known for use in this type of agents. For example, a lubricant, e.g., calcium stearate or magnesium stearate, may be added to a dispersble powder or a mixture to be granulated. "Adhesives", for example, polyvinylalcohol cellulose derivatives or other colloidal materials, such as casein, may also be added so as to improve the adhesion of the presticide to the crop. Furthermore, a substance may be added to reduce the phytotoxicity of the active substance, carrier material or auxiliary substance, for example, wool fat or wool fatty alcohol.

Pesticidal compounds known per se may also be incorporated in the compositions according to the invention. As a result of this the activity spectrum of the composition is widened and synergism may occur.

For use in such a combination composition are to be considered the following known insecticidal, acaricidal and fungicidal compounds.

INSECTICIDES
FOR EXAMPLE 1. organic chlorine compounds, for example 6,7,8,9,10,10-hexachloro-1,5,5a,6,9,9a-hexahydro-6,9-methano-2,4,3-benzo[e]-dioxathiepine-3-oxide;
2. carbamates, for example, 2-dimethylamino-5,6-dimethylpyrimidin-4-yl dimethyl carbamate and 2-isopropoxyphenyl methylcarbamate;
3. di(m)ethylphosphates, for example, 2-chloro-2-diethylcarbamoyl-1-methylvinyl—, 2-methoxycarbonyl-1-methylvinyl—, 2-chloro-1-(2,4-dichlorophenyl)-vinyl—, and 2-chloro-1-(2,4,5-trichlorophenyl)vinyl di(m)ethyl phosphate;
4. O,O-di(m)ethyl phosphorothioates, for example, O(S)-2-methylthioethyl—, S-2-ethylsulphinylethyl—, S-2-(1-methylcarbamoylethylthio)ethyl—, O-4-bromo-2,5-dichlorophenyl—, O-3,5,6-trichloro-2-pyridyl—, O-2-isopropyl-6-methylpyrimidin-4-yl—, and O-4-nitrophenyl O,O-di(m)ethyl phosphorothioate;
5. O,O-di(m)ethyl phosphorodithioates, for example, S-methylcarbamoylmethyl—, S-2-ethylthioethyl—, S-(3,4-dihydro-4-oxobenzo[d]-1,2,3-triazin-3-ylmethyl)—, S-1,2-di(ethoxycarbonyl)ethyl—, S-6-chloro-2-oxobenzoxazolin-3-ylmethyl—, and S-2,3-dihydro-5-methoxy-2-oxo-1,3,4-thiadiazol-3-ylmethyl O,O-di(m)ethylphosphorodithioate;
6. phosphonates, for example, dimethyl 2,2,2-trichloro-1-hydroxyethylphosphonate;
7. natural and synthetic pyrethroids;
8. amidines, for example, N'-(2-methyl-4-chlorophenyl)-N,N-dimethylformamidine;
9. microbial insecticides, such as Bacillus thuringiensis;
10. carbamoyl-oximes, such as S-methyl N-(methylcarbamoyloxy) thioacetamidate; and
11. other benzoylurea compounds, such as N-(2,6-difluorobenzoyl)-N'-(4-chlorophenyl)urea.

ACARICIDES
FOR EXAMPLE 1. organic tin compounds, for example, tricyclohexyl tin hydroxide and di[tri-(2-methyl-2-phenylpropyl)tin]oxide;
2. organic halogen compounds, for example isopropyl 4,4'-dibromobenzilate, 2,2,2-trichloro-1,1-di(4-chlorophenyl)ethanol and 2,4,5,4'-tetrachlorodiphenyl sulphone;
3. synthetic pyrethroids, and furthermore: 3-chloro-α-ethoxyimino-2,6-dimethoxybenzyl benzoate and O,O-dimethyl S-methylcarbamoyl methyl phosphorothioate.

FUNGICIDES
FOR EXAMPLE 1. organic tin compounds, for example, triphenyl tin hydroxide and triphenyl tin acetate;
2. alkylene bisdithiocarbamates, for example, zinc ethylenebisdithiocarbamate and manganese ethylene bisdithiocarbamate;
3. 1-acyl- or 1-carbamoyl-N-benzimidazole (−2) carbamates and 1,2-bis (3-alkoxycarbonyl-2-thiureido)benzene, and furthermore 2,4-dinitro-6-(2-octylphenylcrotonate), 1-[bis(dimethylamino) phosphoryl]-3-phenyl-5-amino-1,2,4-triazole, N-chloromethylthiophthalimide, N-trichloromethylthiotetrahydrophthalimide, N-(1,1,2,2-tetrachloroethylthio)-tetrahydrophthalimide, N-di-chlorofluoromethylthio-N-phenyl-N,N'-dimethylsulphamide, tetrachloroisophthalonitrile, 2-(4'-thiazolyl)-benzimidazole, 5-butyl-2-ethylamino-6-methylpyrimidine-4-yl-dimethylsulphamate, 1-(4-chlorophenoxy)-3,3-dimethyl-1(1,2,4-triazole-1-yl)-2-butanone, α-(2-chlorophenyl)-α-(4-chlorophenyl)-5-pyrimidinemethanol, 1-(isopropylcarbamoyl)-3-(3,5-dichlorophenyl)hydantoin, N-(1,1,2,2-tetrachloroethylthio)-4-cyclohexene-1,2-carboximidine, N-trichloromethylmercapto-4-cyclohexene-1,2-dicarboximidine, N-tridecyl-2,6-dimethylmorpholine.

The dosages of the pesticidal composition according to the invention desired for practical application will, of course, depend on various factors, for example, application area, selected active substance, form or composition, nature and extent of the infection, and the weater conditions.

In general it holds that favourable results are achieved with a dosage corresponding to 1 to 5000 g of the active substance per hectare.

For the above-described "through-feeding" the active substance is mixed through the food in a quantity which is effective for insecticidal application.

The compounds according to the invention are new substances whcih can be prepared in a manner known per se for related compounds.

For example, the compounds according to the invention can be prepared by reacting a substituted aniline of the general formula

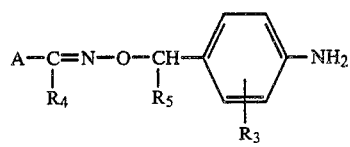

wherein $R_3$, $R_4$, $R_5$ and A have the above-mentioned meanings, with a compound of the general formula

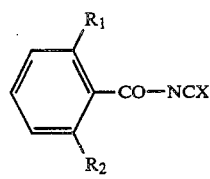

wherein $R_1$, $R_2$ and X also have the above-mentioned meanings.

The new compounds according to the invention can also be prepared by reacting a substituted benzamide of the general formula

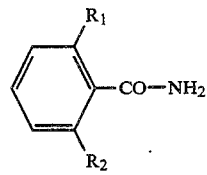

wherein $R_1$ and $R_2$ have the above-mentioned meanings, with a compound of the general formula

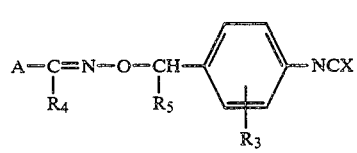

wherein $R_3$, $R_4$, $R_5$, X and A also have the above-mentioned meanings.

The above reactions are preferably carried out in the presence of an organic solvent, such as an aromatic hydrocarbon, an alkyl halide, a cyclic or not cyclic dialyl ether, or acetonitril, at a reaction temperature between 0° C. and the boiling point of the solvent used.

Although the above-indicated methods of preparing are the best suitable, the new compounds can also be prepared in a different manner, for example, as described in the above-mentioned Netherlands patent application No. 7105350 or according to the methods described in the Netherlands patent applications Nos 7806678 or 8005588.

The invention will now be described in more detail with reference to the following specific examples.

EXAMPLE I

Preparation of
N-(2,6-difluorobenzoyl)-N′-[4-(α-cyclopropyl-4-chlorobenzylideneaminooxymethyl)phenyl]urea (1).

36.6 g of 2,6-difluorobenzoylisocyanate in 50 ml of dry diethyl ether were added to a solution of 59.0 g 4-(α-cyclopropyl-4-chlorobenzylideneaminooxymethyl)aniline in 700 ml of dry diethylether with external cooling at 0°-10° C. After stirring for 3 hours at 0°-10° C. the formed precipitate was sucked off, washed with diethyl ether, and dried. The product obtained in a yield of 76.0 g was chromatographed over silica, chloroform being used as an eluent. The desired product was isolated in a yield of 60,7 g having a purity of at least 95% (PMR). The product obtained had a melting range of 145°-175° C. and comprised the syn- and anti-form in approximately equal amounts. In another experiment the desired product was obtained as a mixture of the syn- and anti-form in a ratio of 85:15; melting point 187°-191° C.

The starting aniline was obtained from the corresponding nitro compound by reduction with hydrogen under the influence of Raney nickel as a catalyst; mixture of ethyl acetate and ethanol in a ratio of 2:1 by volume was used as a solvent. 1-Nitro-4-(α-cyclopropyl-4-chlorobenzylideneaminooxymethyl)benzene was prepared by a reaction of (4-chlorophenyl)-cyclopropylketoneoxime with 4-nitrobenzylbromide in methanol as a solvent in the presence of sodium methoxide. The reaction can also be carried out under the influence of sodiumhydride as a base in dimethylformamide as a solvent. The oxime used was obtained from the corresponding ketone by a reaction with hydroxylamine. HCl in a mixture of water and ethanol and under the influence of NaOH.

In a corresponding manner, in which, if desired, instead of diethyl ether acetonitrile was used as a solvent for the urea-formation, the following compounds were prepared;

The compound numbers correspond with the numbers given before in the specification:

| compound no. | melting point | remarks |
| --- | --- | --- |
| 2 | 120–122° C. | |
| 3 | 106,5–108,5° C. | |
| 4 | 144,5–146,5° C. | |
| 5 | 114–117° C. | mixture syn-anti |

-continued

| compound no. | melting point | remarks |
|---|---|---|
| 6 | 144–159° C. | |
| 7 | 141–143° C. | |
| 8 | 141–144,5° C. | |
| 9 | 154,5–157,5° C. | |
| 10 | 203–208° C. | |
| 11 | 113–116° C. | anti-form |
| 12 | 124–132° C. | syn- or anti-form |
| 13 | 153–155° C. | syn- or anti-form |
| 14 | 128–130° C. | syn- or anti-form |
| 15 | 139,5–141,5° C. | |
| 16 | 128–130° C. | |
| 17 | 182–187° C. | mixture syn-anti |
| 18 | 176–180° C. | |
| 19 | 112–114° C. | |
| 20 | 150–152° C. | |
| 21 | 158–160° C. | |
| 22 | 109–112° C. | |
| 23 | 142–147° C. | |
| 24 | viscous liquid* | 23% anti-, 67% syn-form |
| 25 | 133–146° C. | |
| 26 | 125–135° C. | |
| 27 | 164–167° C. | |
| 28 | 162–164° C. | |
| 29 | 158–161° C. | |
| 30 | 130–135° C. | |
| 31 | 130–138° C. | |
| 32 | 207–210° C. | |
| 33 | 107° C. | |
| 34 | 117° C. | |
| 35 | 137° C. | |
| 36 | 153–161° C. | |

*note:
compound no. 24: PMR (CDCl$_3$) syn: $\delta$ (NH) 12, 22; 9,20; anti: $\delta$ (NH) 12, 28; 9,15.

In case this has been determined, it has been stated in the above survey whether the substance obtained is one of the both stereoisomers or a mixture of both. A considerable melting range generally points to a mixture of stereoisomers.

The above compounds could also be obtained easily by starting from substituted benzamides and substituted benzylideneaminooxymethylphenyl isocyanates; same reaction conditions as above. The starting phenyl isocyanates were prepared from the corresponding anilines by a reaction with phosgene in an inert organic solvent, e.g. aromatic solvent like toluene; reaction temperature 0° C. and the boiling point of the solvent. So compound no (1) could be prepared from 2,6-difluorobenzamide and 4-($\alpha$-cyclopropyl-4-chlorobenzylideneaminooxymethyl)phenyl isocyanate in dry diethylether at 0°–10° C. in a yield of approximately 70%.

EXAMPLE II (a) Preparation of a solution of an active substance, viz. N-(2,6-difluorobenzoyl)-N'-[4-($\alpha$-cyclopropyl-4-chlorobenzylidene-aminooxymethyl)phenyl]urea, in a water-miscible liquid ("liquid")

10 g of the above active substance were dissolved in a mixture of 10 ml of isophorone and approximately 70 ml of dimethylformamide, after which polyoxyethylene glycol ricinyl ether was added as an emulsifier in a quantity of 10 g.

In a corresponding manner the other active substances were processed to 10 or 20% "liquids".

In a corresponding manner "liquids" were obtained in N-methylpyrrolidone, dimethylformamide, and a mixture of N-methylpyrrolidone and isophorone as solvents.

(b) Preparation of a solution of the active substance in an organic solvent.

200 mg of the active substance to be tested were dissolved in 1,000 ml of acetone in the presence of 1.6 g of nonylphenolpolyoxyethylene. After pouring out into water this solution can be used as a spray liquid.

(c) Preparation of an emulsifiable concentrate of the active substance 10 g of the active substance to be tested were dissolved in a mixture of 15 ml of isophorone and 70 ml of xylene; to this solution were added 5 g of a mixture of a polyoxyethylene sorbitan ester and an alkyl benzene sulphonate as an emulsifier.

(d) Preparation of a dispersible powder (WP) of the active substance.

125 g of the active substance to be tested were mixed with 68 g of kaolin in the presence of 2 g of sodium butylnaphthalene sulphonate and 5 g of lignine sulphonate.

(e) Preparation of a suspension concentrate (flowable) of the active substance

A mixture of 10 g of the active substance, 2 g of lignine sulphonate and 0.8 g of a sodium alkylsulphate were supplied with water till a total amount of 100 ml.

(f) Preparation of a granule of the active substance 7.5 g of the active substance, 5 g of sulphite lye and 87.5 g of ground dolomite were mixed, after which the resulting mixture was processed to a granular composition by means of the so-called compacting method.

EXAMPLE III

Young Brussels sprouts plants, approximately 15 cm high, were sprayed with compositions obtained according to Example II (b) in various concentraions; in addition approximtely 250 mg of an alkylated phenolpolyoxyethelene compound (Citowett) per litre had been added to these compositions. After the plants had dried up, they were placed in plexiglass cylinders and then infected with 5 larvae of Pieris brassicae (caterpillars of the cabbage white butterfly) in the third larval stage (L3). The cylinders were then covered with a gauze and stored, an alternating light-dark cycle of 16 hours light and 8 hours dark being used; temperature in the light 24° C., relative humidity (RH) 70%, temperature in the dark 19° C., 80–90% RH. After 5 days the mortality percentage of the larvae was established. Each experiment has been carried out in triplicate. The average results of the experiments are recorded in table A below. The meanings of the symbols indicated in the table are as follows:

+ = 90–100% mortality
± = 50–90% mortality
− = <50% mortality.

TABLE A

| Insecticidal activity against larvae (L3) of Pieris brassicae | | | | | | | | |
|---|---|---|---|---|---|---|---|---|
| concentration in mg of active ingredient per liter | | | | | | | | |
| Compound no. | 300 | 100 | 30 | 10 | 3 | 1 | 0,3 | 0,1 | 0,03 |
| 1 | + | + | + | + | + | + | + | ± | − |
| 17 | + | + | + | + | + | + | − | | |

TABLE A-continued

Insecticidal activity against larvae (L3) of *Pieris brassicae*

| Compound no. | concentration in mg of active ingredient per liter | | | | | | | | |
|---|---|---|---|---|---|---|---|---|---|
| | 300 | 100 | 30 | 10 | 3 | 1 | 0,3 | 0,1 | 0,03 |
| 18 | + | + | + | + | + | + | + | ± | − |
| 19 | + | + | + | + | + | + | − | | |
| 20 | + | + | + | + | + | + | + | + | − |
| 3 | + | + | + | + | + | + | − | | |
| 4 | + | + | + | + | + | + | ± | − | |
| 5 | + | + | + | + | + | + | − | | |
| 6 | + | + | + | + | + | + | + | ± | − |
| 7 | + | + | + | + | + | + | − | | |
| 8 | + | + | + | + | + | + | + | − | |
| 10 | + | + | + | + | + | + | + | − | |
| 11 | + | + | + | + | + | + | − | | |
| 12 | + | + | + | + | + | + | + | − | |
| 14 | + | + | + | + | + | + | + | ± | − |
| 15 | + | + | + | + | + | + | − | | |
| 16 | + | + | + | + | + | + | ± | | |
| 21 | + | + | + | + | + | + | − | | |
| 22 | + | + | + | + | + | + | + | − | |
| 23 | + | + | + | + | + | + | + | + | − |
| 24 | + | + | + | + | + | + | ± | − | |
| 25 | + | + | + | + | + | + | − | | |
| 26 | + | + | + | + | + | + | − | | |
| 27 | + | + | + | + | + | + | − | | |
| 29 | + | + | + | + | + | + | − | | |
| 30 | + | + | + | + | + | + | − | | |
| 33 | + | + | + | + | + | + | − | | |
| 34 | + | + | + | + | + | + | + | ± | − |
| 35 | + | + | + | + | + | + | ± | − | |
| 36 | + | + | + | + | + | + | − | | |

In practice insecticidal and acaricidal compositions are used in quantities of approximately 100 liters per hectare. The coverage of the plants with the composition, however, is considerably less in practice than in a laboratory or greenhouse experiment as described above. Accordingly, it has proven that in practice the dosage should be improved with a factor of 10 to achieve the same efficiency. Therefore in practical application the above quantities with insecticidal activity correspond with approximately 1 to 3000 grams of active substance per hectare.

EXAMPLE IV

Young potato plants, approximately 15 cm high, were sprayed with the compositions obtained according to Example II (b) in various concentrations; in addition approximately 250 mg of Citowett per liter had been added to these compositions. After the plant had dried-up, plexiglass cylinders were placed over the plants. The plants were then infected with 10 larvae of *Leptinotarsa decemlineata* (larvae of the Colorado beetle) in the third larval stage (L3). The infected plants were stored as indicated in Example III. After 5 days the mortality percentage of the larvae was established. The experiments have been carried out in triplicate. The average results of the experiments are recorded in table B below. The meanings of the symbols are the same as in Example III.

TABLE B

Insecticidal activity against larvae of *Leptinotarsa decemlineata*

| Compound no. | concentration in mg of active ingredient per liter | | | | | | |
|---|---|---|---|---|---|---|---|
| | 300 | 100 | 30 | 10 | 3 | 1 | 0,3 |
| 1 | + | + | + | + | + | ± | − |
| 23 | + | + | + | + | + | ± | − |

In practice the above quantities with insecticidal activity correspond with approximately 10 to approximately 3000 grams of active substance per hectare.

EXAMPLE V

The growth tips of broad bean plants having four well developed leaves were removed, after which the plants were sprayed until dripping with compositions obtained according to Example II (b) in various concentrations; in addition approximately 250 mg of Citowett per liter had been added to these compositions. After the plants had dried-up, they were placed in perspex cylinders and then infected with 5 larvae of *Spodoptera littoralis* (Egyptian cotton caterpillar) in the third larval stage (L3). The cylinders were then covered with a gauze and then stored as indicated in Example III. After 5 days the mortality percentage of the larvae was established. Each experiment was carried out in triplicate. The average results of the experiments are recorded in Table C. The meanings of the symbols are the same as in Example III.

TABLE C

Insecticial acitivity against larvae (L3) of *Spodoptera littoralis*

| Compound no. | concentration in mg of active ingredient per liter | | | | | | |
|---|---|---|---|---|---|---|---|
| | 300 | 100 | 30 | 10 | 3 | 1 | 0,3 |
| 1 | + | + | + | + | + | + | − |
| 17 | + | + | + | + | ± | − | |
| 19 | + | + | ± | ± | − | | |
| 3 | + | + | + | + | − | | |
| 4 | + | + | + | + | ± | − | |
| 5 | + | + | + | + | − | | |
| 6 | + | + | + | + | ± | − | |
| 7 | + | + | + | + | + | − | |
| 8 | + | + | + | + | + | − | |
| 9 | + | + | + | + | + | − | |
| 14 | + | + | + | + | ± | − | |
| 22 | + | + | + | + | − | | |
| 23 | + | + | + | + | − | | |
| 24 | + | + | + | ± | − | | |
| 28 | + | + | + | + | + | − | |
| 29 | + | + | + | + | + | − | |
| 30 | + | + | + | + | + | ± | − |
| 33 | + | + | + | + | ± | − | |
| 34 | + | + | + | + | ± | − | |
| 35 | + | + | + | ± | ± | ± | − |
| 36 | + | + | + | + | ± | − | |

In practice the above quantities with insecticidal activity correspond with approximately 3 to approximately 1000 grams of active substance per hectare.

EXAMPLE VI

Dwarf French bean plants (*Phaseolus vulgaris*) having two well developed leaves were infected with *Tetranychus cinnabarinus* (carnation spider mite) by placing a fixed number of adult female mites on the plants. Two days after the infection the plants with the adult mites present thereon were sprayed until dripping with compositions obtained according to Example II (b) in various concentrations; in addition approximately 150 mg of an alkylated phenolpolyoxyethylene compound (Citowett) per liter had been added. Five days after the spraying the adult mites were removed from the plants. The plants were stored during two weeks in a room with controlled temperature (T) and humidity (RH), an alternating light-dark cycle of 16 hours light and 8 hours dark being used. Light: T approximately 24° C., RH approximaely 70%; dark: T approximately 19° C., RH 80-90%. Then the reduction of the population, i.e. the mortality of the number of larvae adults and eggs in comparison with plants which are not treated with chemicals, was established. The experiments were carried out in triplicate. The average results of the experiments are recorded in Table D below. The meanings of the symbols used in the table are as follows:

+ = 90-100% reduction of the population; plants free or substantially free from spider mites;
± = 50-90% reduction of the population;
− = <50% reduction of the population.

N-(2,6-difluorobenzoyl)-N'-(4-benzyloxphenyl)urea ("known") has been included in the tests by way of comparison.

TABLE D

Activity against *Tetranychus cinnabarinus* (carnation spider mite)

| Compund no. | concentration in mg of active ingredient per liter | | | | | | |
|---|---|---|---|---|---|---|---|
|  | 300 | 100 | 30 | 10 | 3 | 1 | 0,3 |
| 1 | + | + | + | + | + | + | − |
| 2 | + | ± | − |  |  |  |  |
| 3 | + | ± | ± | − |  |  |  |
| 4 | + | + | + | ± | − |  |  |
| 5 | + | ± | − |  |  |  |  |
| 6 | + | + | ± |  |  |  |  |
| 7 | + | ± | − |  |  |  |  |
| 8 | + | + | + | + | + | + | − |
| 9 | + | + | + | + | − |  |  |
| 10 | + | + | ± | ± |  |  |  |
| 13 | + | ± | ± | − |  |  |  |
| 14 | + | + | + | + | ± | − |  |
| 16 | + |  |  |  |  |  |  |
| 17 | + | + | + | + | − |  |  |
| 21 | + | ± | − |  |  |  |  |
| "known" | − |  |  |  |  |  |  |

In practice the above quantities with acaricidal activity correspond with approximately 10 to approximately 3000 grams of active substance per hectare.

Repetitions of the above experiments, wherein the adult mites are removed prior to the spraying (Method A), or wherein the spraying was carried out prior to the infection (Method B), yielded about the same results.

EXAMPLE VII

In the same way as described in Example VI, method A, benzoylurea compounds according to the invention were tested on *Panonychus ulmi* (European red mite). The results are recorded in Table E, wherein the symbols have the same meanings as in Example VI.

TABLE E

Activity against *Panonychus ulmi* (European red mite)

| Compound no. | concentration in mg of active ingredient per liter | | | | | | |
|---|---|---|---|---|---|---|---|
|  | 300 | 100 | 30 | 10 | 3 | 1 | 0,3 |
| 1 | + | + | + | + | + | ± | − |
| 4 | + | + | + | + | − |  |  |
| 2 | + | + | + |  |  |  |  |
| 3 | + | + | + |  |  |  |  |
| 5 | + | + | + |  |  |  |  |
| 6 | + | + | + | + | + | − |  |
| 7 | + | + | + | + | ± | − |  |
| 8 | + | + | + | + | ± | − |  |
| 9 | + | + | + | + | + | − |  |
| 15 | + | + | + |  |  |  |  |
| 16 | + |  |  |  |  |  |  |
| 17 | + | + | + |  |  |  |  |
| 36 | + | + | + | + | + | − |  |

The same results were obtained, when the spraying was carried out prior to the infection (method B).

Liquid compositions are applied on fruit-trees in quantities of approximately 1500 liters per hectare. Then the above quantities with acaricidal activity correspond in practice with approximately 150 to approximately 4500 grams of active substance per hectare.

EXAMPLE VIII

In the same way as indicated in Example VI, method A, N-(2,6-difluorobenzoyl)-N'-[4-(α-cyclopropyl-4-chlorobenzylideneaminooxymethyl)phenyl]urea (1) was tested on *Tetranychus urticae* (two-spotted spider mite), giving the results recorded in Table F. Again the meanings of the symbols are the same as in Example VI.

TABLE F

Activity against *Tetranychus urticae* (two-spotted spider mite)

| Compound no. | concentration in mg of active ingredient per liter | | | | | |
|---|---|---|---|---|---|---|
|  | 300 | 100 | 30 | 10 | 3 | 1 |
| 1 | + | + | + | + | + | − |

About the same results were obtained, when the experiments were carried out on a multiresistent strain of *Tetranychus urticae*.

In practice the above quantities with acaricidal activity correspond with approximately 30 to approximately 3000 grams of active substance per hectare.

EXAMPLE IX

Dwarf French bean plants (*Phaseolus vulgaris*) having two well developed leaves were sprayed from below and from above until dripping with a composition prepared according to Example II (a); in addition 150 mg of Citowett per liter had been added to this composition. The composition comprised N-(2,6-difluorobenzoyl)-N'-[4-(α-cyclopropyl-4-chlorobenzylideneaminooxymethyl)phenyl]urea (1) as the active substance in various concentrations. After the plants had dried-up they were infected with mites of a multiresistent strain of *Tetranychus urticae* (two-spotted spider mite) in the same way as described in Example VI. The experiments were carried out outdoors. After a fixed number of days (see Table G) the reduction of the population with respect to infected plant material, which was not sprayed with a composition, was estimated. The experiments were carried out five-fold; the series of experiments were repeated ("rep." in Table G). The average results per test series are recorded in Table G.

TABLE G

Acaricidal activity against *Tetranychus urticae*

| concentration in mg active ingredient per liter | mortality %, 1st series, after 16 days | mortality %, rep.; after 24 days |
|---|---|---|
| 100 | 100 | 100 |
| 30 | 95 | 100 |
| 10 | 89 | 100 |

The quantities indicated in Table G correspond with approximately 10 to approximately 1000 grams of active substance per hectare under practical conditions.

EXAMPLE X

Apple trees, headed on 40 cm, were sprayed from below from above until dripping with a composition prepared according to Example II (a); in addition 250 mg of an alkylated phenolpolyoxyethylene compound (Neutronix) per liter had been added to this composition. The composition comprised a benzoylurea compound according to the invention as an active substance. The apple trees were infected previously as described in Example VI with *Aculus schlechtendali* (apple rust mite), and at the moment of spraying the mites were present in all development-stages. After 2 and 4 weeks outdoors the reduction of the population of the mites was established. The experiments were carried out sixfold. The average results are recorded in Table H.

TABLE H

| | Acaricidal activity against *Aculus schlechtendali* | | |
| --- | --- | --- | --- |
| Compound no. | concentration in mg of active ingredient per liter | reduction of the population after 2 wks | after 4 wks |
| 1 | 100 | 98 | 97 |
| | 30 | 97 | 95 |
| 4 | 100 | 80 | 57 |
| | 30 | 63 | 34 |
| untreated | — | 0 | 0 |

EXAMPLE XI

Inhibition of the growth of tumor cells

After pre-incubation at 37° C. during 3 hours the compound to be tested was added in an amount of 5000 ppm to B 16 melanoma cells, growing as a monolayer on a growing medium. The experiment was carried out in triplicate. The mixture was then incubated at 37° C. during 20 hours. After removal of the growing-medium and the test-compound the cells were washed and fresh growing-medium was added. The amount of cells was determined 48 hours after the beginning of the incubation period with a microcell Coulter Counter. Compound no. (1) caused 53% inhibition of the cell growth compared to an experiment without a test-compound.

We claim:

1. A composition having insecticidal and acaricidal activity, comprises a liquid or solid inert carrier material and a insecticidally and acaricidally effective amount of an active constituent of the following formula I:

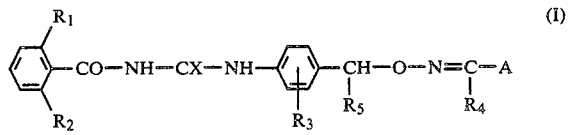

wherein $R_1$ is a halogen atom, $R_2$ *is a hydrogen atom or a halogen atom,*

$R_3$ is a hydrogen atom or represents 1 or 2 substituents which are selected from the group consisting of chlorine, methyl and trifluoromethyl, $R_4$ is a hydrogen atom, an alkyl group having 1–6 carbons atoms or a cycloalkyl group having 3–6 carbon atoms, $R_5$ is a hydrogen atom or an alkyl group having 1–4 carbon atoms, A is a phenyl group or a heteroaryl group having 1 or 2 nitrogen atoms, which groups may be substituted with 1–3 substituents which are selected from the group consisting of halogen, and alkyl, alkoxy, haloalkyl and haloalkoxy having 1–4 carbon atoms, and X is an oxygen or sulphur atom.

2. A composition as claimed in claim 1, wherein the active constituent is a compound of the formula II:

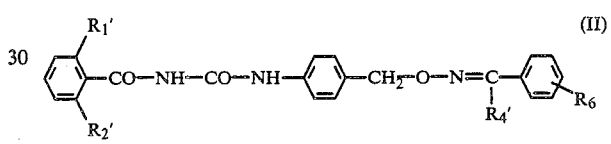

wherein $R_1'$ and $R_2'$ are both fluorine atoms, or wherein $R_1'$ is a chlorine atom and $R_2'$ is a hydrogen atom, $R_4'$ is a n-propyl, isopropyl or cyclopropyl group, and $R_6$ is hydrogen atom or represents 1–2 substituents which are selected from the group consisting of halogen, and alkyl, alkoxy, haloalkyl and haloalkoxy having 1–4 carbon atoms.

3. A composition as claimed in claim 1, wherein the active constituent is N-(2,6-difluorobenzoyl)-N-[4-(α-cyclopropyl-4-chlorobenzylideneaminooxymethyl)-phenyl]urea.

4. A method of controlling insects and mites, wherein the infected area is treated with a composition as claimed in any one of claims 1, 2, or 3 in a dosage from 1 to 5000 g of active substance per hectare.

* * * * *